United States Patent [19]
Harada

[11] Patent Number: 4,878,378
[45] Date of Patent: Nov. 7, 1989

[54] ROTATING VISCOMETER

[75] Inventor: Manabu Harada, Tokyo, Japan

[73] Assignee: Kabushiki Kaisha Marukomu, Tokyo, Japan

[21] Appl. No.: 181,474

[22] Filed: Feb. 3, 1988

Related U.S. Application Data

[63] Continuation-in-part of Ser. No. 7,342, Jan. 28, 1987, abandoned.

[30] Foreign Application Priority Data

Jan. 29, 1986 [JP]  Japan ............................. 61-11422[U]

[51] Int. Cl.⁴ ........................................... G01N 11/14
[52] U.S. Cl. ....................................................... 73/59
[58] Field of Search ................................ 73/59, 60, 54

[56] References Cited

U.S. PATENT DOCUMENTS

| | | | |
|---|---|---|---|
| 2,491,423 | 5/1949 | Gisser | 73/9 |
| 2,953,682 | 9/1960 | Frank et al. | 73/59 |
| 2,992,651 | 7/1961 | Krofta | 73/59 |
| 3,115,769 | 12/1963 | Bowen, Jr. | 73/59 |
| 3,229,506 | 1/1966 | Bruss et al. | 73/59 |
| 4,077,251 | 3/1978 | Winter | 73/59 |
| 4,334,424 | 6/1982 | Kepes | 73/59 |

FOREIGN PATENT DOCUMENTS

| | | | |
|---|---|---|---|
| 1254887 | 11/1967 | Fed. Rep. of Germany | 73/59 |
| 823977 | 4/1981 | U.S.S.R. | 73/59 |

Primary Examiner—Hezron E. Williams
Attorney, Agent, or Firm—Robert F. Ziems

[57] ABSTRACT

A rotating viscometer for a paste is constructed of a rotary member, a stationary member provided in opposition to the rotary member with a small clearance therebetween, said stationary member being displaceable angularly relative to the rotary member, a paste inlet formed in communication with the small clearance to allow the paste to flow into the small clearance upon rotation of the rotary member relative to the stationary member, a paste outlet for allowing the paste to flow out of the small clearance, and a means for sensing a torque applied to the stationary member owing to the viscosity of the paste introduced in the small clearance by the rotation of the rotary member.

15 Claims, 4 Drawing Sheets

ROTATING VISCOMETER

CROSS-REFERENCE TO RELATED APPLICATION

This application is a continuation in part of copending application Ser. No. 007,342, filed Jan. 28, 1987, abandoned.

BACKGROUND OF THE INVENTION

1. Field of the Invention

This invention relates to a rotating viscometer capable of accurate measurement of fluid viscosity for both Newtonian and non-Newtonian fluids, and which is operative with small amounts of such fluids. The rotating viscometer is suited especially for use with a screen printing machine and is designed in such a way that it allows measurement and control of the viscosity of a fluid, such as paste, immediately before it is coated over a substrate by the printing machine. The viscosity of such fluids can be specified and precise control over ,the viscosity of the fluid can be achieved by maintaining the fluid shearing time constant while continuously kneading the fluid. As a result of these features, the rotating viscometer of this invention enables accurate screen printing.

2. Description of the Prior Art

There is an ever-increasing demand for the densification and hybridization of electronic devices in this age of electronics. According to the hybrid microelectronics technology which has been developed to meet that demand, active elements equipped with various functions are packaged in combination with passive elements such as resistors, capacitors and the like on a substrate to materialize a light, thin, short and small hybrid IC module.

In the fabrication of a hybrid IC modules, a substrate is first printed using a screen printing machine. The substrate is printed in this manner with various pastes such as conductive paste, resistive paste, dielectric paste and solder paste, a resist ink, and inks of other functional materials. This printing work requires a high degree of accuracy because of the nature of the hybrid IC module. In such printing work, the accuracy of printed film thickness and patterns is heavily dependent on the accuracy of control of various functions of the screen printing machine.

A controlled variable which is considered to be most important to increased accuracy of printing, but which is regarded as a variable difficult to control, is the viscosity of a paste (ink), itself. As a result, the difficulties in controlling the viscosity of the paste are dealt with by relying on the experience of printing technicians and laboratory measurements in may instances.

The difficulties encountered in controlling the viscosities of pastes can be attributed to the fact that many pastes, behave as non-Newtonian fluids, have thixotropic properties and are hence affected by surrounding conditions such as temperature and humidity. Moreover, the viscosities of such fluids do not remain constant either during or after kneading. Even if the viscosity of a paste is measured by a viscometer after its kneading, the paste is fed to a screen printing machine subsequent to its kneading to a desired viscosity and a substrate is then printed with the-thus fed paste, the viscosity of the paste changes moment by moment and does not remain stable during the printing work so that no accurate screen printing work is feasible. Moreover, the paste is kneaded further by a squeegee (i.e., a doctor blade for coating the paste) during the printing work. This additional kneading renders the viscosity of the paste more unstable, thereby making it difficult, if not impossible, to perform accurate screen printing.

Viscometers which have conventionally been employed for screen printing are rotating viscometers, because they are also employed to knead pastes stored in tanks. Specifically, the rotational resistance of each rotating viscometers is recorded as a viscosity. Because of the kneading work performed, the conventional viscometers are relatively large and expensive. Also in the use of such rotating viscometers, the viscosity of a paste in a tank is measured as if it was done in a laboratory. It is impossible to measure the viscosity of a paste at the point of application by a screen printing machine. Since the viscosity of the paste cannot be measured and controlled accurately, no precise screen printing can be expected.

As mentioned above, the pastes used in the fabrication of hybrid IC modules have properties of non-Newtonian fluids so that the viscosities of the pastes vary considerably depending on temperature. In addition, the viscosity, of the paste changes significantly in accordance with the speed and time of shearing the paste by the rotary member. For these reasons, the measurement of the paste viscosity in the past was periodically effected at a fixed interval, for example, at every third minute by using a stopwatch. While this approach to viscosity measurement may appear to be accurate, it requires measurement of the viscosity of the whole of a large amount of a paste being kneaded. Otherwise, its viscosity cannot be accurately determined. In addition, the viscosity must be measured repeatedly many times. The above method is hence accompanied by further drawbacks that the viscosity of the paste cannot be measured continuously, the measurement of the viscosity cannot be automated, the efficiency of the measurement is low, and measurement of the viscosity is cumbersome.

Thus a major problem in the measurement and regulation of paste viscosity in prior methods for fabricating hybrid IC modules is that the shearing time cannot be maintained constant. In this respect, it has been attempted to measure the viscosity of a paste while recirculating the paste forcibly through the shearing gap of rotating double-cup-type viscosimeter. This approach, however, (1) requires complex system for the forced recirculation, leading to excessive viscosimeter and expense; (2) the recirculating force affects the torque produced to measure the viscosity of the paste, thus reducing accuracy of the viscosity measurement; (3) when gravity forced recirculation is employed, the shearing time varies; and (4) the forced recirculation method requires a larger flow passage for the recirculation of the paste, again leading to the drawback that the rotating viscometer itself becomes large and expensive.

SUMMARY OF THE INVENTION

An object of this invention is to meet the demand for improved accuracy in screen printing, specifically, to provide a rotating viscometer which is small in size and capable of high accuracy so that an accurate measurement of viscosity of a paste can be made immediately prior to its application to a substrate by a screen printing machine. Another object is the provision of such a viscosimeter which can be manufactured at a low cost, and which assures that the shearing time of a fluid, such as paste, always remains constant even if the fluid demonstrates non-Newtonian behavior and even whole the fluid is being kneaded, whereby the viscosity of the fluid can be specified and the accurate viscosity of the fluid can hence be measured and controlled automatically.

In the case of a non-Newtonian fluid like paste in particular, its viscosity generally changes with shearing time, Its viscosity therefore varies as it is sheared in a viscometer. It is thus necessary to specify the measurement time for the determination of this viscosity. With the foregoing in view, another object of this invention is to provide a rotating viscometer in which the rotation of a cylinder to knead the paste automatically draws the paste upward at a constant shearing speed (i.e., at a constant revolution speed) and discharges the paste upon lapse of a constant time interval to achieve constant shearing time; and even in the case of a fluid the viscosity of which depends on the shearing time, such as a paste, its viscosity can be measured continuously and accurately.

The specification of a viscometer, which can fulfill the above-described requirement for its application on a screen printing machine, namely, permits measurement of the viscosity of a paste moving on the screen printing machine while being kneaded thereon, includes:

(1) the measurement of the viscosity of the paste is not affected by its flow caused by its movement and kneading;

(2) in order to investigate the thixotropic properties and flow curve of the paste, the revolution speed of the rotary member can be varied over a wide range, for example, from 1 rpm to 100 rpm;

(3) the measurement of the viscosity of the paste can be effected without need for inserting the rotary member in its entirety in the paste;

(4) the measurement of the viscosity of the paste can be achieved even with a very small sample of the paste;

(5) the viscometer is durable;

(6) the viscometer is small;

(7) the viscometer is inexpensive; and (8) the shearing time of the paste can be maintained constant even while the paste is being kneaded, and as a result, the viscosity of the paste can be specified.

The rotating viscometer useful on the screen printing machine must satisfy such contradictory requirements.

The requirement (1) is needed in order to measure accurately the viscosity of the paste on the screen printing machine, in other words, is needed from the use conditions inherent to screen printing.

The requirement (2) is needed to accommodate the properties of the highly-viscous paste employed in screen printing and having properties of non-Newtonian fluids.

The requirements (3) and (4) are needed to measure the viscosity of the small amount of the paste on the screen printing machine accurately at its point of application to a substrate.

The requirement (5) is needed because the viscometer is moved frequently on the screen printing machine while measuring the viscosity.

The requirement (6) is needed from the limitation in space that similar to the requirement (5), the viscometer has to be arranged on the screen printing machine to measure the viscosity of the paste on the screen printing machine.

The requirement (7) is an obvious need upon producing goods. In the case of screen printing machines in particular, the low manufacturing cost leads to screen printing machines having a high market value.

The requirement (8) allows control of the shearing time, namely, to maintain constant the measuring time of the paste viscosity. The viscosity can hence be specified, thereby permitting automatic, accurate, prompt and easy measurement and control of the viscosity.

In one aspect of this invention, there is thus provided a rotating viscometer comprising:

a rotary member provided rotatably at a constant speed;

a stationary member provided in opposition to the rotary member with a small clearance therebetween, said stationary member being displaceable angularly relative to the rotary member;

a paste inlet formed in communication with the small clearance to allow a paste to flow into the small clearance upon rotation of the rotary member relative to the stationary member;

a paste outlet for allowing the paste to flow out of the small clearance; and a means for sensing a torque applied to the stationary member owing to the viscosity of the paste introduced in the small clearance by the rotation of the rotary member.

The rotating viscometer of this invention can bring about the following practical effects:

(1) According to the rotating viscometer of this invention, the viscosity of the paste, especially, the viscosity of the paste immediately prior to its printing on a substrate can be measured with good accuracy even if the amount of the paste on the screen printing machine is small or the paste has the properties of non-Newtonian fluids and thixotropic properties. It is hence possible to conduct high-accuracy screen printing.

(2) Since the viscosity of the paste immediately prior to its printing can be measured on the screen printing machine as described in the advantage (1), the use of the rotating viscometer of this invention in a screen printing machine, as opposed to the measurement of the viscosity of a paste stored only in a tank in the main body of the screen printing machine, is not affected by subsequent flow of the paste and hence permits screen printing of higher accuracy than conventional viscometers.

For a reduced manufacturing cost, it is possible to omit the system for the measurement of the viscosity of the paste in the tank, which is included in a conventional screen printing machine, and to use only the rotating viscometer of this invention, thereby materializing an economical screen printing machine.

A high-accuracy screen printing machine can also be materialized at a low cost if the rotating viscometer of this invention and a necessary controller are added as an accessory to a conventional screen printing machine equipped with no viscosity control system.

(3) The rotating viscometer of this invention can measure the viscosity of a fluid by inserting only a part of the viscometer, for example, a tip portion thereof in the fluid. It is therefore possible to measure the viscosity of a fluid in such a small amount that conventional rotating viscometers are difficult to measure, for example, the viscosity of a small amount of a paste on a screen printing machine as described above.

Accordingly, the use of a rotating viscometer of this invention on a screen printing machine makes it unnecessary to build an expensive and large rotating viscometer in the main body of a screen printing machine like conventional screen printing machines.

The rotating viscometer of this invention allows higher freedom in the arrangement of the paste tank than in the conventional design in which the paste is stored within each screen printing machine, whereby the rotating viscometer of this invention contributes to versatility of screen printing machines with various shapes and various prices.

(4) Since the rotating viscometer of this invention permits the viscosity measurement of a small amount of a fluid such as paste, it can measure the viscosities of more fluids such as pastes arranged in various forms than conventional rotating viscometers.

(5) Because the rotating viscometer of this invention permits the viscosity measurement of a small amount of a fluid such as paste, the viscosity measurement is not affected by the flow of the fluid which is moving while being kneaded.

(6) The rotating viscometer has such a structure that the revolution speed of its rotary member can be changed over a wide range, for example, from 1 rpm to 100 rpm. It is hence possible to investigate with ease the thixotropic properties and flow curve of a fluid such as paste, whereby a high-accuracy viscosity control is feasible.

(7) According to the rotating viscometer of this invention, it is possible to control the time period from the introduction of a fluid such as paste, which is continuously kneaded, until its discharge, or in other words to maintain a constant the shearing time. The rotating viscometer of this invention can therefore measure and control its viscosity accurately. Especially, the viscosity of a non-Newtonian fluid such as paste generally varies in accordance with its shearing time. Its viscosity must thus be determined by specifying the measuring time. In the rotating viscometer of this invention, the paste is automatically drawn into the viscometer upon rotation of the member for kneading the paste. At a constant shearing velocity (i.e., at a constant revolution speed), the paste is discharged after a lapse of a constant period of time and is then recirculated continuously. It is therefore possible to maintain constant the time period during which the paste is subjected to shearing within the main body of the rotating viscometer, thereby assuring a constant shearing time, Even in the case of a fluid the viscosity of which is dependent on its shearing time, such as a paste, its viscosity can be measured continuously and accurately.

(8) Finally, the rotating viscometer of this invention features a small, inexpensive and durable structure.

BRIEF DESCRIPTION OF THE DRAWINGS

The above and other objects, features and advantages of this invention will become apparent from the following description and the appended claims, taken in conjunction with the accompanying drawings, in which:

DETAILED DESCRIPTION OF THE INVENTION AND PREFERRED EMBODIMENTS

Figure 1:
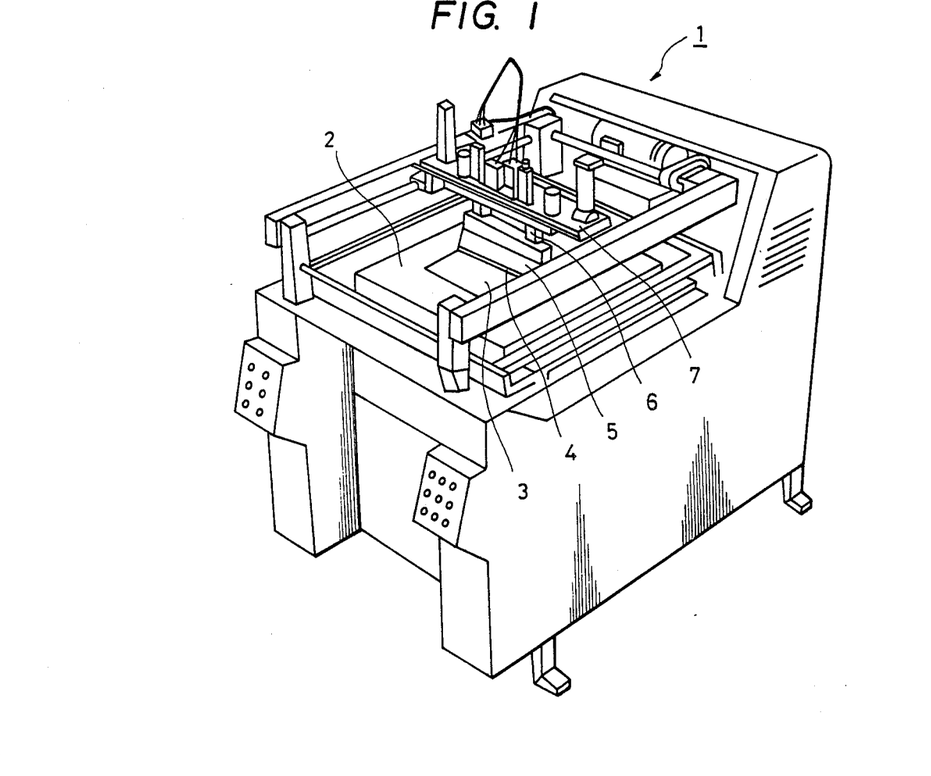
FIG. 1 is a schematic perspective view of a screen printing machine.

In FIG. 1 which is a schematic perspective view of a screen printing machine numerals 2 and 3 designate a substrate table and a substrate, respectively. The substrate 3 is fixed on the substrate table 2 by means of an unillustrated fixing member. Designated by numeral 4 is a squeegee, which is supported by a support member 5. The support member 5 is in turn secured on squeegee carriage 7 by a fixing member 6 which also serve as feed pipes.

Figure 2:
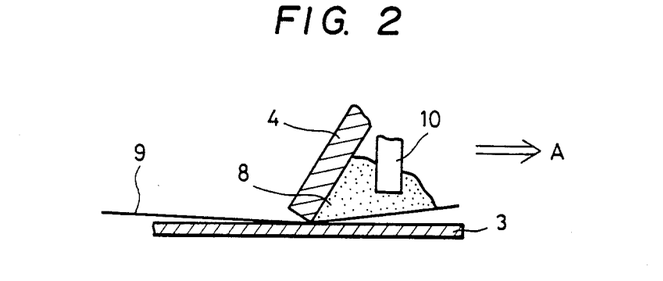
FIG. 2 is an enlarged fragmentary view of a paste-coating part including a squeegee.

In the illustrated screen printing machine 1, the squeegee 4 also serves as a return blade for a paste 8 (see, FIG. 2). When the squeegee 4 functions as the return blade, the squeegee 4 is lifted at the turn, shifted automatically to a position from which the return of the paste is started, and then lowered. Upon backward movement of the squeegee 4, the paste is drawn back.

The structure of the screen printing machine is, however, not necessarily limited to that shown. As an alternative, a return blade may be provided as a member discrete from the squeegee 4.

FIG. 2 illustrates on an enlarged scale a part of the screen printing machine 1 where the paste 8 is applied by the squeegee 4. When the squeegee carriage 7 is caused to move in the direction indicated by the arrow A by means of an unillustrated motor, the squeegee 4 also advances in the direction indicated by the arrow A so that the substrate 3 is coated with the paste 8 through a screen 9.

The paste 8 is stored in a tank within the main body of the printing machine 1 and is kneaded to a suitable viscosity. A suitable amount of the paste 8 is fed to the rear side (on the side of the arrow A) of the squeegee 4 by way of the feed pipe and fixing member 6 and support member 5.

In the paste 8 on the rear side of the squeegee 4, a tip portion of a rotating viscometer 10 of this invention is inserted. The rotating viscometer 10 will be described in detail below. The rotating viscometer 10 is provided at a suitable position so that its tip portion can be inserted in the paste 8. For example, the rotating viscometer 10 may be provided on the rear wall of the squeegee 4, or on a member disposed in the proximity of the squeegee 4, for example, the support member 4, fixing member 6 or carriage 7, or on a return blade.

The squeegee 4 is designed in such a way that its inclination and its pressure against the upper surface of the substrate 3 can be adjusted by signals from an unillustrated controller.

The rotating viscometer 10 of the present invention is of the radial clearance type and will be described in more detail below. Rotating viscometers such as viscotester and Brookfield viscometer are known as this general type of viscometer. Such conventional rotating viscometers, however, cannot be used in printing machines of the kind described above because the nature of the viscosity measurement of the paste 8 on the screen 9, namely, as the viscosity measurement is conducted while the paste 8 is moving and is being kneaded.

Moreover, conventional rotating viscometers which are commercially available are of a design intended to measure the viscosity of a large quantity of fluid. For example, the fluid in a tank is kneaded and the viscosity of the fluid itself is measured while continuing the kneading of the fluid. Such conventional rotating viscometers cannot, however, determine the viscosity of a small quantity of fluid and where the fluid changes considerably in viscosity like the paste 8 on the screen printing machine 1.

Since commercially-available rotating viscometers have been used alone in screen printing machines, the paste 8 is kneaded in an unillustrated tank where the paste is stored. The viscosity of the thus-kneaded paste is then measured. When the viscosity of the paste 8 appears to become constant, the thus-kneaded paste 8 is merely fed to the rear side of the squeegee 4 by a suitable means without accounting in any way for viscosity changes in the paste constantly on the screen printing machine 1 as a result of the paste 8 being a non-Newtonian fluid having a high viscosity.

The small and economical rotating viscometer 10 of the present invention, therefore, while of radial clearance type, is suited for the measurement of the viscosity of the paste 8 on the screen printing machine 1 even if the amount of the paste 8 is small. The rotating viscometer 10 of this invention is therefore different in principle from conventional rotating viscometers.

Figure 3:
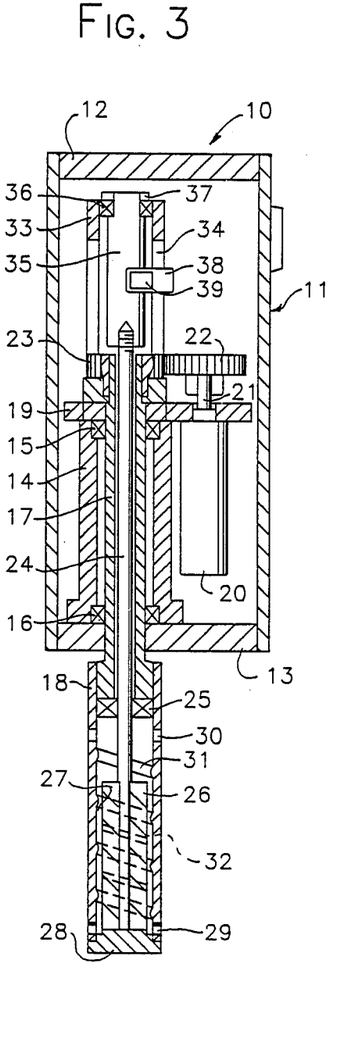
FIG. 3 is a vertical cross-sectional view of a rotating viscometer according to the first embodiment of this invention.

In FIG. 3, one embodiment of the rotating viscometer 10 is shown to include a main body 11 which is in the form of a hollow rectangular housing, closed at the upper opening thereof by an upper cover 12 and at the lower opening thereof by a lower cover 13 with a hole extending therethrough. A cylindrical bearing housing 14 is fixed on the lower cover 13. Ball bearings 15,16 are provided respectively at edge portions of the bearing housing 14, which edge portions define upper and lower openings of the bearing housing 14. The ball bearings 15,16 rotatably support a hollow rotary shaft 17.

A lower end portion of the rotary shaft 17 extends out through the cover 13. A rotary cylinder 18 is fixed on the outer periphery of the thus-extending lower end portion of the rotary shaft 17 so that the rotary cylinder 18 is allowed to rotate together with the rotary shaft 17.

On the top of the bearing housing 14, a mounting plate 19 is fixed. A geared motor 20 is fixedly mounted on the mounting plate 19. A gear 22 is secured on the drive shaft 21 of the geared motor 20. The gear 22 is maintained in meshing engagement with a gear 23 secured on the rotary shaft 17.

A shaft 24 is inserted in the hollow spacing of the rotary shaft 17. A lower end portion of the shaft 24 is rotatably supported by a ball bearing 25 provided on an upper part of the inner peripheral wall of the rotary cylinder 18.

A stationary cylindrical block 26 is fixed on a lower end portion of the shaft 24. A small annular clearance 27 which is adapted to allow the paste 8 to flow therethrough is formed between the cylinder block 26 and the rotary cylinder 18.

A cover 28 is fixed over the lower end opening of the rotary cylinder 18 so as to close the lower end opening. The rotary cylinder 18 defines at a lower end portion thereof a paste inlet 29 through which the paste 8 flows into the clearance 27. Instead of providing this form of paste inlet 29, it may be possible to omit the cover 28 and to draw up the paste 8 directly through the lower end of the clearance 27.

The rotary cylinder 18 also defines at an upper end portion thereof a paste outlet 30 for discharging the paste 8, which has flowed into the clearance 27 through the paste inlet 29, out of the rotary cylinder 18.

In the embodiment illustrated in FIG. 3, the cylindrical block 26 is provided as a stationary member and the rotary cylinder surrounding the cylindrical block 26 is rotated. This structure has an advantage that the cylindrical block 26 is protected by the outer rotary cylinder 18 so as to shield the cylindrical block 26 from the flowing force of the paste 8 present outside the viscometer.

Figure 4:
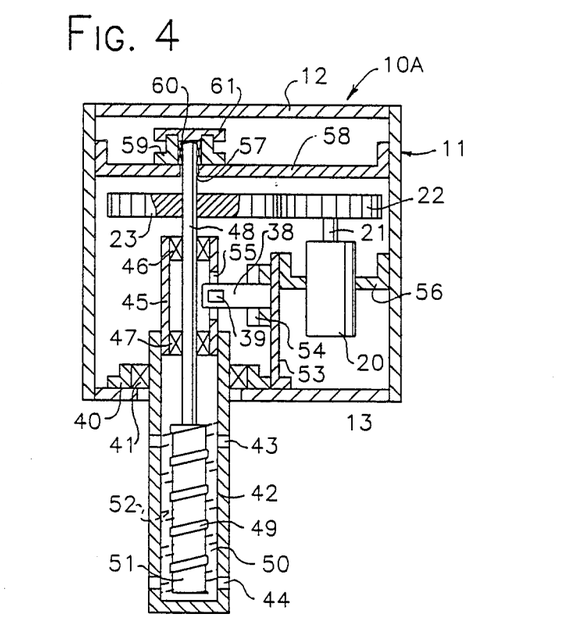
FIG. 4 is a vertical cross-sectional view of a rotating viscometer according to the second embodiment of this invention.

In order to protect a rotary member from external forces, it is possible to adopt the structure shown in FIG. 4 in which an outer cylinder is provided as a stationary member while an inner cylindrical block serves as a rotary member.

It is to be noted that the described rotary cylinder 18 is not required to be exclusively cylindrical in shape. It may take any shape so long as the highly viscous paste 8 is caused to ascend through the clearance 27 formed as a paste flow passage between the rotary cylinder 18 an the cylindrical block 25 and to flow out of the clearance 27 through the paste outlet 30 when the rotary cylinder 18 is rotated. Similarly, the shape of the cylindrical block 26 is not necessarily limited may be, changed from that shown.

It is important that the clearance 27 is formed as a radial gap through which the paste 8 is caused to ascend upon rotation of the rotary cylinder 18. The paste 8 is caused to ascend through the clearance 27 upon rotation of the rotary cylinder as described above, because the paste 8 is a fluid having a high viscosity. It is difficult for a low-viscosity fluid such as plain water to ascend through the clearance 27.

It is a characteristic feature of the rotating viscometer 10 of this invention that the high viscosity of the paste is utilized to allow the paste 8 to ascend through the clearance 27. It is another characteristic feature of the rotating viscometer 10 that after the measurement, the paste 8 which has flowed up through the clearance 27 is discharged so as to allow the paste 8 to flow back to its original position.

In order to ensure the ascent of the paste 8 through the clearance 27 of such a small width, a relatively wide spiral groove 31 having a shallow depth may be formed in the clearance-defining surface of the rotary cylinder 18 so as to cause the upward flow of the paste 8. Instead of the spiral groove 31 formed in the clearance-defining surface of the rotary cylinder 18, a spiral groove 32 may be formed in the outer surface of the cylindrical block 26 as shown by dotted lines.

As a further alternative, both spiral grooves 31,32 may be formed. The direction of the spiral turn of each of these spiral grooves 31,32 is set in such a way that the upward flow of the paste 8 is promoted by the rotation of the rotary cylinder 18. The lead angle of the spiral turn is preferably small, usually, at an angle of 10 degrees or smaller, preferably at an angle of 5 degrees or smaller, for example, 3 degrees.

A cylindrical bearing housing 33 is mounted fixedly on the mounting plate 19. The bearing housing 33 defines at a portion thereof a slit 34 which serves as a stopper for a leaf spring to be described.

A detection shaft 35 is fixed on an upper end portion of the shaft 24. The detection shaft 35 is supported rotatably by a ball bearing 36 provided on the inner peripheral wall of an upper end opening of the bearing housing 33. At an upper portion of the bearing housing 33, there is fixed a stop ring 37 for the prevention of vertical vibrations of the detection shaft 35. Unless the vertical (i.e., axial) movement of the detection shaft 35 is limited by a certain means, it is impossible to obtain accurate signals from a resistance strain gage 39 to be described.

Designated at numeral 38 is a leaf spring, which is secured at one end thereof with an adhesive or the like on the outer peripheral wall of the detection shaft 35 and is inserted at the other end thereof in the slit 34 formed in the bearing housing 33. The resistance strain gage 39 is provided on the outer wall of the leaf spring 38 so as to convert torques of the detection shaft 35 into changes in resistance.

As the resistance strain gage 39, a suitable gage such as piezoelectric element, pressure sensitive element or strain gage may be used. In the first embodiment, a strain gage is used.

FIG. 4 illustrates a rotating viscometer 10A according to another embodiment of this invention. Different from the rotating viscometer 10 of the first embodiment, the outer member serves as a stationary member while the member provided inside the outer member acts as a rotary member.

The upper end opening and lower end opening of the fixed main body 11 of the rotating viscometer 10A are also closed by the upper cover 12 and lower cover 13 respectively. A bearing housing 40 is fixed on the lower cover 13. A stationary cylinder 42 is supported by a ball bearing 41 provided on the bearing housing 40 in such a way that the stationary cylinder 42 is allowed to undergo angular displacement relative to a rotary columnar block 49 to be described subsequently. The lower end of the stationary cylinder 42 is closed by an integral cover.

A paste outlet 43 is formed through the stationary cylinder 42 at a location spaced from the lower cover 13. A paste inlet 44 is formed through a lower end portion of the stationary cylinder 42. A cylinder detection member 45 is fixed in an upper end portion of the stationary cylinder 42. At both upper and lower end openings of the detection member 45, a rotary shaft 48 is supported rotatably by ball bearings 46,47.

A rotary columnar bock 49 is fixedly suspended from the lower end of the rotary shaft 48. Thus, a clearance 50 is formed as a paste flow passage between the rotary columnar block 49 and stationary cylinder 42.

In order to facilitate the upward flow of the paste 5, which has flowed into the clearance 50 through the paste inlet 44 and has properties like non-Newtonian fluids of high viscosity, through the clearance 50 upon rotation of the rotary columnar block 49, a spiral groove 51 is formed in the outer peripheral surface of the rotary columnar block 49 along the central axis of the rotary columnar block 49.

As a modification, instead of the spiral groove 51, a spiral groove 52 may be formed in the inner peripheral surface of the stationary cylinder 42 along the central axis of the stationary cylinder 42 as indicated by dotted lines in order to facilitate the upward flow of the paste.

As another modification, both spiral grooves 51,52 may be provided in combination.

A mounting plate 53 is mounted upright on the lower cover 13. A fixing member 54 is in turn secured on the mounting plate 53. The leaf spring 38 is cemented at one end thereof on the fixing member 54.

A slit 55 is formed in a part of the side wall of the detection member 45. The other end of the leaf spring 38 is inserted in the slit 55. On the outer surface of the leaf spring 38, the resistance strain gage 39 is secured.

Between the fixing plate 53 and the main body 1, a mounting plate 56 extends horizontally as viewed on FIG. 4. The geared motor 20 is fixed on the mounting plate 56. The gear 22 is fixed on the drive shaft 21 of the geared motor 20. The gear 22 is maintained in meshing engagement with the gear 23 secured on the rotary shaft 48.

On the inner wall of the main body 11 and above the gears 22,23, a fixing plate 58 defining a throughhole 57 is fixedly provided horizontally across the main body 11. A bearing housing 59 is fixed concentrically with the through-hole 57 n the fixing plate 58.

The rotary shaft 48 is rotatably supported at an upper end portion thereof by a ball bearing 60, which is provided on the inner peripheral wall of the bearing housing 59. A stopper cap 61 is fixedly screwed on the upper end of the baring housing 59, whereby the rotary shaft 48 is preventing from vibrating in the vertical direction.

In the viscometers 10,10A, the detection shafts 35,48, namely, the stationary cylindrical block 26 and the rotary columnar block 49 are prevented form undergoing vertical vibrations owing to the provision of the stopper ring 37 and stopper cap 61. Therefore, the length of the flow passage of the paste 8 is maintained constant and highly reliable results are obtained. In addition, the resistance strain gage 39 is also prevented from undergoing vertical vibrations.

When the rotating viscometer 10 or 10A is applied to the above-described screen printing machine 1, it is operated in the following manner. The paste 8 is fed through the feed member 6 onto the screen 9. While moving the squeegee carriage 7, i.e., the squeegee 4 in the direction the paste 8 is applied onto the substrate 3 through the screen 9 as shown in FIG. 2. The rotary cylinder 18 of the viscometer 10 or the stationary cylindrical body 42 of the viscometer 10A is inserted at its tip portion into the paste 8 until the paste inlet 29 or 44 is submerged under the paste 8. When the geared motor 20 is continuously driven, the gear 22 is rotated and the gear 23, which meshes with the gear 22, is then rotated. Thus, the rotary shaft 17 or 48 on which the gear 23 is fixed rotates in the same direction as the gear 23.

Upon rotation of the rotary shaft 17 or 48, the rotary cylinder 18 or rotary columnar block 49 which is fixed on the rotary shaft 17 or 48 is rotated relative to the stationary cylindrical block 26 or stationary cylinder 42.

When the rotary cylinder 18 or rotary columnar block 49 rotates, the paste 8 having properties similar to high-viscosity non-Newtonian fluids is drawn upwards through the paste inlet 29 or 44 into the clearance 27 or 50 as the paste flow passage. While being assisted by the spiral groove 32 (and/or 32) or 51 (and/or 52), the paste 8 is allowed to flow upwards through the clearance 27 or 50.

As the paste ascends through the clearance 27 or 50 in the above-described manner, the paste 8 is discharged through the paste outlet 30 or 43 formed through the upper part of the rotary cylinder or stationary cylinder 42. The paste 8 then flows down along the outer peripheral wall of the rotary cylinder 18 or stationary cylinder 42 to its initial position, namely, the position where the paste 8 is supposed to exist upon its viscosity measurement.

As the paste flows upwards through the clearance 27 or 50, a torque, the magnitude of which is dependent on the viscosity of the paste in the clearance 27 or 50, is applied in the direction of the rotary member to the stationary cylindrical block 26 or stationary cylinder 42. In the viscometer shown in FIG. 3, the detection shaft 35 undergoes an angular displacement in the same direction as the stationary cylindrical block 26 and shaft 24 against the leaf spring 38 inserted at one end thereof in the slit 37. As a result, the leaf spring 38 is flexed. Since the degree of this deformation of the leaf spring 38 is proportional to the magnitude of the torque applied to the rotary member, an electrical signal is output from the resistance strain gage 39. This electrical signal is employed as a signal representing the viscosity of the paste 8. In the viscometer of FIG. 4 on the other hand, the detection member 45 rotates against the leaf spring 38 inserted in the slit 55. As a result, the leaf spring 38 is bent and similar to the viscometer of FIG. 3, as signal representing the viscosity of the paste 8 is obtained form the resistance strain gage 39.

For a full understanding of the present invention and the principle of viscosity measurement effected by its practice, a review of the fluid viscosity fundamentals will be helpful. In this respect, the behavior of a fluid in a narrow annular gap between relatively rotatable inner and outer cylinders must be considered.

If the outer cylinder is rotated at a peripheral speed of v with a stress of $\tau$, while the inner cylinder is held stationary, a velocity gradient D is generated in the fluid. Also, forces that accelerate and decelerate are generated in the fluid. The cause of the generation of these forces is called viscosity. If the space between cylinders is infinitesimal, the viscosity is equal to $\tau$, and its magnitude is in proportion to the velocity gradient $D = v/y$. This proportionality constant is defined as the coefficient of viscosity $\eta$. Accordingly, $$\text{Coefficient } \eta = \frac{\tau}{D} \frac{(\text{dyn cm}^{-2})}{(S^{-1})} \text{ dyn s cm}^{-2} \quad (1)$$

In this expression, D and $\tau$ are called the shear rate and shear stress respectively. As the unit of viscosity coefficient, P (poise) and PaO−s (Pascal second) are used. $1\text{Pa}-\text{s} = 10^3\text{mPa}-\text{s} = 10^3\text{cP} = a0\text{P}$.

Figure 5:
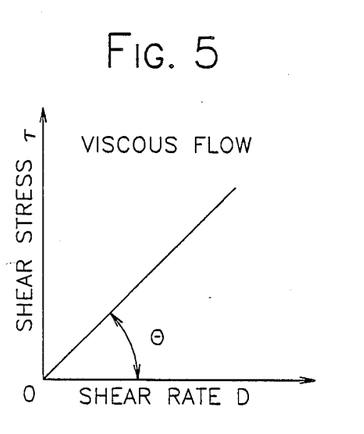
FIGS. 5 and 6 are flow curves for Newtonian and non-Newtonian fluids respectively.

If values of shear rate (D) are plotted against values of shear stress ($\tau$), a flow curve is developed. A fluid which initiates flow even when $\tau$ is infinitely small and whose viscosity coefficient is constant regardless of the magnitude of D is called a Newtonian fluid because it obeys Newton's law. The viscosity flow curve shown in FIG. 5 corresponds to it. $\eta = \tan \theta$.

Figure 6:
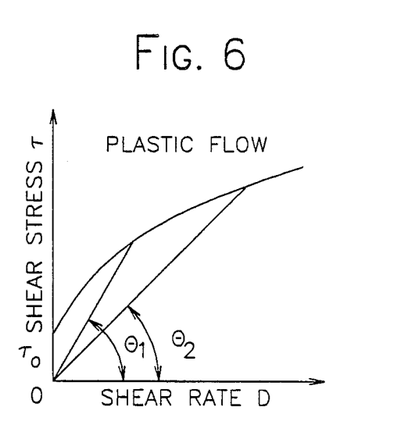

However, generally ink and paste do not exhibit Newtonian properties. Most of them exhibit the plastic flow shown in FIG. 6 or the pseudo-plastic flow of $\tau_o = 0$, and when the shear rate D is 0, a stress with a magnitude of the yield value $\tau_o$ shown in the figure is necessary. That is, the flow cannot occur unless a force of $\tau_o$ or more is applied. Also, the viscosity coefficient $\eta = \tau/D$ is not constant as the shear rate D changes. From the figure it is seen that $\eta_1 > \eta_2$ at $\eta_1 = \tan \theta_1$ and $\eta_2 = \tan \theta_2$. $\eta_1$ and $\eta_2$ are called the apparent viscosity of a non-Newtonian fluid. In the case of non-Newtonian fluid, viscosity of meaningless if the shear rate D is not specified. Hereafter, the apparent viscosity will also be called viscosity.

When ink and paste are exposed to a strong shear stress on a roller or screen, they are softened by the destruction of the vehicle layer on the surface of the particles. When it is left alone, the viscosity recovers as the vehicle layer regenerates. This property is called thixotropy. The time taken from destruction until recovery is in some cases nil, while some pastes taken one day or even one week to recover.

The principle of the rotating cylinder viscometer is based upon the shearing of paste, so the measurement involves a continuous process of structure destruction and regeneration of paste. Therefore for a thixotropic fluid which requires a longer recovery time, the viscometer acts as a stirrer, and the viscosity value measured becomes a function of time. Accordingly, the viscosity of paste has:

a. shear rate dependency; and
b. shear time dependency.

Therefore, the measurement is meaningless if the shear rate and shear time are not specified. Also, as a matter of course, the influence of temperature should be taken into consideration.

Figure 7:
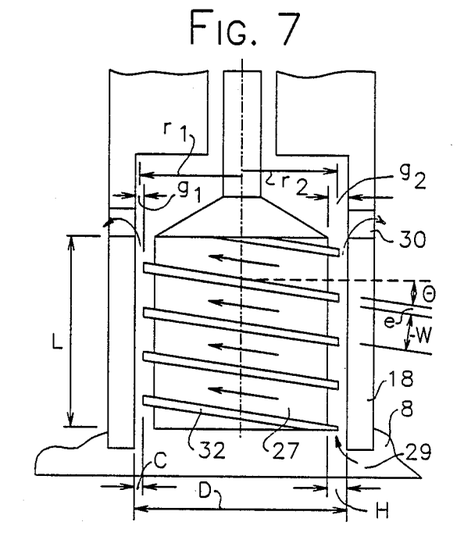
FIG. 7 is a schematic view depicting various parameters of the embodiment of FIG. 4.

In FIG. 7, an embodiment of the present invention similar to that of FIG. 3 is represented schematically and shown to include a rotatable outer cylinder 18 and a stationary inner cylinder 27 with spiral flutes 32. The sample 8 in the gap between the inner and outer cylinders 27, 18 and in the spiral flutes 32 enters from a charging port 29, moves up the flutes and is discharged through ports 30 as the outer cylinder 18 rotates. As this movement of the sample 8 occurs, the shear stress received by the sample 8 is detected as the torque M received by the inner cylinder 27. This value divided by the angular velocity N of the outer cylinder 18 is proportional to the viscosity $\eta$ of the sample. The relations between $\eta$ and N, and between T, which is the time necessary for movement of the sample through the gap between the inner and outer cylinder, and N are described below.

The state of the fluid which moves around the spiral gap shown in FIG. 7 is made clear by the analysis method of fluid mechanics. In FIG. 7, c and H are the small gaps between the spiral flutes 32 and roots, and the inner wall of the outer cylinder 18. W is the width of the thread passage, e is the width of the flutes 32 and $\theta$ is the very small lead angle of the spiral.

Although the several dimensions indicated in FIG. 7 may vary widely with adaptation of the viscometer of the present invention to diverse applications and with the characteristics of the fluids to be measured for viscosity, in a working embodiment like that of FIG. 7 where the viscosity of the sample 8 is expected to be equal to or greater than 50 poise, the dimensions shown in FIG. 7 may be quantified as follows: D=1.2 cm, L=2.5 cm, H=0.12 cm, c=0.04 cm, $\theta = 5°$, e=0.05 cm, and W=0.25 cm. The total length of the spiral (designated to be hereinafter by the latter Z) is 28.4 cm.

Figure 8A:
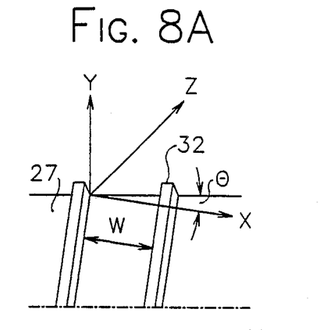
FIGS. 8A and 8B are vector diagrams applicable to the embodiment of FIG. 4.
Figure 8B:
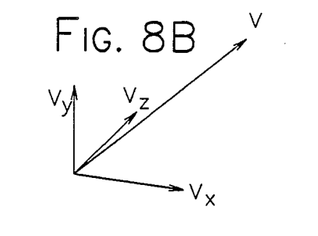

When for the convenience of analysis the position of the spiral flutes is described with rectangular coordinates shown in FIGS. 8A and 8B, the passage of the root becomes parallel with the Z axis, and the x and y axes become parallel with the width and height of the passage cross section with maximum values of W and H, respectively. If the flow-velocity vector of any point in this passage is V ($v_x$, $v_y$, $v_z$), the direction of fluid passage, that is, the Z axis component $v_z$, is the component which decides the amount of flow Q.

Accordingly, the amount of flow Q is the integral value of $v_z$ at the xy surface.

$$Q = \int_0^H \int_0^W v_z dx dy \quad (2)$$

In Navier-Stokes' equation of motion, a basic equation of fluid mechanics, if a flow steady flow due to high viscosity flow is supposed and if the fluid pressure is P, the following equation can be obtained:

$$\frac{1}{\eta} \frac{\partial P}{\partial z} = \frac{\partial^2 V_z}{\partial x^2} + \frac{\partial^2 V_z}{\partial y^2} \quad (3)$$

As a result of the adjustment, taking into account the influence of the gap and each boundary condition of passage, the solution of $v_z$ can be obtained (omitted). When this solution is substituted in equation (1), the flow amount Q is:

$$Q = \alpha N - \frac{\beta \Delta P}{\eta Z} \quad (4)$$

In this equation, N is the angular velocity of the outer cylinder 18a, and $\beta$ are shape factors which affect the pumping characteristics of the device and which are determined by the parameters C, H, W $\theta$, etc., Z is the total passage length of the spiral, $\Delta P$ is the pressure difference between the entry port 19a and the exit port 30a for the fluid, $\Delta P = 980 \rho L \sin \theta$, and $\rho$ is the specific gravity of the fluid.

In this connection, the constants of a working embodiment of the sensor depicted in FIG. 7 with the exemplary dimensions given above are approximately $\alpha = 1.4 \times 10^{-2}$, $\beta = 3.3 \times 10^{-5}$, Z = 28.4 cm, $\Delta P = 213.5$ dyncm$^{-2}$. Accordingly, when N > 1 RPM, $\eta$ > 50P, then the function $\delta N$ is much greater than the function $$\frac{\beta \Delta P}{\eta Z}$$

and largely determinative of the amount of flow Q. In practice using the exemplary embodiment of FIG. 7, the angular velocity N approximates 10 RPM. Also, when the time in which the fluid in the gap entirely moves is T seconds, and the cross section of passage is S, from the equation (4) the shear time T is:

$$T = \frac{SZ}{\alpha} \cdot \frac{1}{N} \quad (5)$$

From equation (5) it can be concluded that the shear time has nothing to do with viscosity and is inversely proportional to only the angular velocity N.

Next, when the Z- and X-axis components of shear stress acting on the xz surface at the inner wall of the outer cylinder or a fluid with a height of y=H are $\tau_{yz}$ and $\tau_{yx}$, and the flow velocities moving to each direction are $V_z$ and $V_x$, then the necessary energy E to turn the inner cylinder is:

$$E = \int_0^Z \int_0^W (\tau_{yx} V_x + \tau_{yz} V_z) dx dz \quad (6)$$

By solving this equation, and by taking into account the energy consumed in the gap between the outer cylinder and the thread, the following equation can be obtained:

$$E = \epsilon N^2 Z + \alpha N \Delta P \quad (7)$$

In this equation $\epsilon$ is the shape factor of the viscometer as determined by such parameters as C, H, W, $\theta$, etc. In the case of a working embodiment of the sensor represented in FIG. 7, when $\epsilon = 44.6$ and the torque working on the outer cylinder is M, $E = 2\pi NM$, and $\epsilon Z N \eta > \alpha \Delta P$. Accordingly, from equation (6) the torque M is:

$$M = \frac{\epsilon Z}{2\pi} N\eta \quad (8)$$

From equation (8), it can be concluded that the torque M is only in proportion to the angular velocity N and viscosity $\eta$, and it has nothing to do with the differential pressure or the flow of fluid.

For pseudo-plastic flow, the following equation is known empirically:

$$D = \frac{1}{K} \tau^n \quad (9)$$

In this equation K is the constant decided by the fluid, and n is a real number of 1 or more.

In the case of a conventional double-cup viscometer (not shown) in which a smooth surfaced outer cylinder of a radius $R_1$ is rotated at a constant velocity N relative to a smooth surfaced inner cylinder of a radius $R_2$ to define a shearing gap of a radius r, the shear rate D which is received by the fluid in the gap of the radius of r is:

$$D = \frac{4\pi N n}{60} \frac{1}{r^{2n}} \frac{R_1^{2n} R_2^{2n}}{R_1^{2n} - R_2^{2n}} \quad (10)$$

If n=1, equation (10) shows the shear rate of the Newtonian fluid. So, in order to examine the distribution of D in the gap, the change curves of D and $\eta$ against radius r are shown in FIG. 9 when the $R_1 = 1.2$ cm, $R_2 = 1.0$ cm and n is a parameter.

Figure 9:
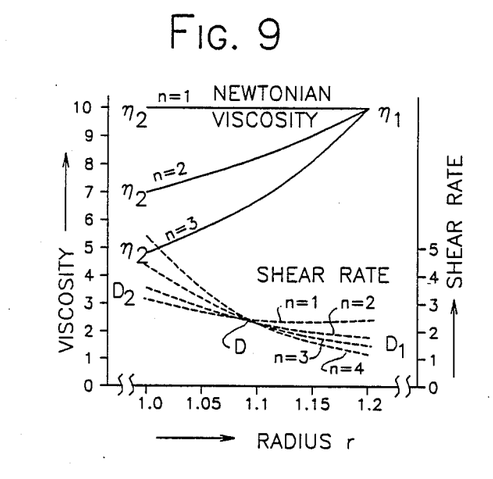
FIG. 9 is a graph showing curves representing the distribution of viscosity and shear rate between inner and outer cylinders of various radii.

From FIG. 9 it can be understood that the average shear rate value when n=1 exists as a shear rate value not influenced by the index n or magnitude of the non-Newtonian flow. In this, the calculation was done based upon a ratio of the radius of the cylinders of 1.2. As the ratio of radius becomes smaller, that is, the gap becomes smaller, the precision of the average shear rate value improves.

Essentially, the principle of viscosity measurement of such a rotating viscometer is based upon the measurement of the viscous torque of the fluid in the gap at a constant angular velocity of the cylinder. Therefore, even if the shear rate is not constant, the viscosity can be calculated if the shear rate can be specified and the radius r at that time is known, because the viscosity torque M in the gap is the same at any point on the radius r.

In the spiral viscometer of the present invention represented in FIG. 7, two gaps $g_1$ and $g_2$ exist between the inner and outer cylinders, and different average shear rates exist in each gap. Accordingly, the torque received by the inner cylinder 27 is the sum of the viscosity torques which are produced by each shear rate. Moreover, the two torques are in proportion to the width e of the spiral thread and the width W of the spiral root, respectively.

If $M_1$=The torque generated at $g_1$; $M_2$=The torque generated at $g_2$; $D_1$=The average shear rate of $g_1$; $D_2$=the average shear rate of $g_2$; $r_1$=The radius to define $D_1$; $r_2$=The radius to define $D_2$; $h_1$=The sum of the thread width of the inner cylinder; $h_2$=The sum of the root width of the inner cylinder; $\eta_1$=The viscosity of $D_1$; $\eta_2$=The viscosity of $D_2$; then the torques developed by the gaps $g_1$ and $g_2$ are:

$$M_1 = 2\pi r_1^2 h_1 \eta_1 D_1; \quad M_2 = 2\pi r_2^2 h_2 \eta_2 D_2$$

The composite torque is:

$$M = M_1 + M_2 = 2\pi r^2 h \eta D \quad (11)$$

In this equation, $\eta$ and D are the average viscosity of the spiral viscometer and the average shear rate respectively.

$$\left(\frac{r_1}{r}\right)^2 = \left(\frac{r_2}{r}\right)^2 = 1.$$

Accordingly, in the case of pseudo-plastic flow, from equations (1) and (9):

$$\eta = K^{\frac{1}{n}} D^{\frac{1}{n}-1}$$

Therefore, from equation (11):

$$D = \left(\frac{h_1}{h} D_1^{\frac{1}{n}} + \frac{h_2}{h} D_2^{\frac{1}{n}}\right) \quad (12)$$

Figure 10:
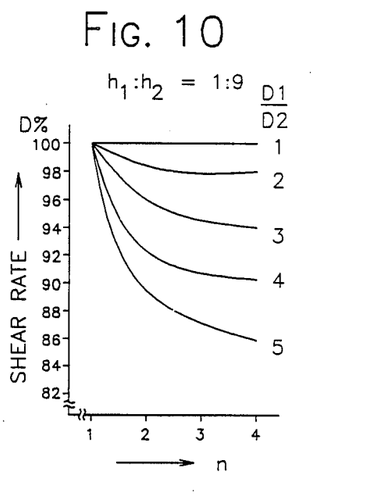
FIG. 10 is a graph showing shear rate error of the viscometer of the present invention for different fluids.

From equation (12) the of the average shear rate D as the index n changes is calculated and is shown in FIG. 10 when the rat of shear rates in the gaps $g_1$ and $g_2$, or $D_1/D_2$, is used as a parameter. From FIG. 10, which represents the shear rate error in terms of percentage deviation from constant shear rate, using the spiral viscometer of the present invention for several fluids, where $D_1/D_2 < 3$, it may be seen that the error of shear rate can be held within 5% when a fluid with n less than 3 is measured. Also, it can be demonstrated in the same way that the error of the shear rate is small when the Bingham flow is measured.

From the foregoing analysis it will be seen that in the viscometer of the present invention, the greater the ratio of the thread root width to the thread flute width or W/e, the more effective the viscometer will be in achieving constant shearing rate because deviation of D to n is kept small enough even when the ratio $D_1/D_2$ (ratio of shearing rates in the gaps $g_1$ and $g_2$) increases to 2, 3 or more due to the characteristics of the liquid to be measured as represented by the value of n. Moreover, the greater the ratio W/e, the more effective the viscometer will be in operation to achieve a steady flow of liquid when the pitch angle $\theta$ is as small as 10° or less because the direction of flow for every part of the flowing liquid can be made coincident uniformly with the direction of the spiral. Accordingly, it is preferred generally that the viscometer be designed so that the value of the ratio W/e is 3 or more, and that the thread pitch $\theta$ is 10° or less. When these design criteria are met, shearing time can be maintained by substantially constant in a wide range of liquid viscosities and angular velocities N, with a provision that the dimensions c and H (FIG. 7) are small and the relation of $$\frac{H}{2} > c > 0.24H$$

is satisfied, thereby achieving a condition where torque detected is proportional to viscosity of the flowing liquid.

In the described embodiments, no reference has been made to the measurement of the temperature of the paste 8. When certain specific types of pastes are used, it may be desired to measure and correct for the temperature of the paste. In such as case, a temperature sensor may be provided on the viscometer in the vicinity of the part to be inserted in the paste 8, for example, near its tip portion (in this case, the temperature sensor may be built in the tip portion) in order to detect the temperature of the paste. A signal representing the temperature of the paste 8 is output from the temperature sensor. It is convenient to amplify the signal by an amplifier and to display the temperature and viscosity of the paste 8 in a real time mode on a paste temperature displayer provided with the rotating viscometer 10 or 10A. If one wants to obtain the viscosity of the paste 8 as a value corrected to a desired temperature, it is convenient to display at the displayer a viscosity temperature-controlled by a temperature correction circuit. As further modifications, it may also be feasible to perform various measurements by providing an additional function to display the viscosity and temperature in a real time mode, a system to preset the upper and lower limits of the viscosity, a function to change the shearing time, etc.

Having now fully described the invention, it will be apparent to one of ordinary skill in the art that many changes and modifications can be made thereto without departing from the spirit or scope of the invention as set forth herein.

I claim:

1. In a rotating viscometer including relatively stationary and rotatable members supported on a common axis, the members having spaced, mutually facing surfaces to define a clearance gap located between the surfaces and extending in generally parallel relation to the surfaces between opposite ends, the improvement comprising:

means defining a fluid inlet at one end of said clearance gap and a fluid outlet at the other end of said clearance gap; and means defining spiral flutes on at least one of said surfaces, said spiral flutes having a pitch angle ($\theta$), a width (e) and being spaced along the length of said clearance gap to define spiral grooves of a width (W) in said one surface;

said pitch angle ($\theta$), flute width (e) and said groove width (W) being selected so that upon movement of the rotatable member relative to the stationary member, fluid introduced at said fluid inlet is advanced through said clearance gap to said fluid outlet under shearing forces for measurement of the viscosity of the fluid and so that the shearing time and shear rate remain substantially constant.

2. The viscometer recited in claim 1 wherein said pitch angle ($\theta$) is less than 10°.

3. The viscometer recited in claim 2 wherein said pitch angle is in the range of between 3° and 5°.

4. The viscometer recited in claim 1 wherein said spiral groove width (W) is at least three times the width (e) of said flutes.

5. The viscometer recited in claim 1 wherein the spacing (c) between said flutes on the one surface and the other surface and the spacing (H) between said spiral grooves on the one surface and the other surface are related so that torque developed between said stationary and rotatable members is proportional to the viscosity of liquid in said clearance gap.

6. The viscometer recited in claim 5 wherein said spacings (c) and (H) are related so that (c) is less than one-half (H) and greater than 0.24 (H).

7. The viscometer recited in claim 1 including means for sensing torque applied to the stationary member due to the viscosity of the paste introduced in the small clearance by the rotation of the rotary member.

8. The rotating viscometer recited in claim 7, wherein the sensing means is a torque-electrical signal transducer which upon application of torque from said stationary member, generates an electrical signal corresponding to the torque.

9. The rotating viscometer as recited in claim 8, wherein the torque-electrical signal transducer is provided on a spring member which is deformed upon application of the torque applied to the stationary member.

10. The rotating viscometer recited in claim 9, wherein the torque-electrical signal transducer is provided on a leaf spring which is fixed at one end thereof on either one of a viscometer housing and the stationary member and upon an angular displacement of the stationary member, the other end of the stationary member is brought into engagement with the other one of the viscometer housing and the stationary member.

11. The rotating viscometer as claimed in claim 10, wherein the torque-electrical signal transducer is a strain gauge.

12. The viscometer recited in claim 1 wherein said mutually facing surfaces are inner and outer cylindrical surfaces concentric with said axis so that the length of said clearance gap is parallel to said axis.

13. The viscometer recited in claim 12 including means for supporting said members at one end thereof, the other end of said members respectively projecting from said supporting means.

14. The viscometer recited in claim 13 wherein said fluid inlet is located near said other end of said members and wherein said fluid outlet is located between said other end and said supporting means.

15. The viscometer recited in claim 12 wherein said inner cylindrical surface is on said rotatable member and said outer cylindrical surface is on said stationary member and wherein said fluid outlet opens through said stationary member.

* * * * *